United States Patent [19]

Homma et al.

[11] 4,096,245

[45] Jun. 20, 1978

[54] PROPHYLACTIC PREPARATION FOR TREATING MINK INFECTION CAUSED BY *PSEUDOMONAS AERUGINOSA*

[75] Inventors: Yuzuru Homma, Tokyo; Takeshi Shimizu, Kodaira; Kazuo Okada, Tokyo, all of Japan

[73] Assignee: President of The University of Tokyo, Tokyo, Japan

[21] Appl. No.: 664,835

[22] Filed: Mar. 8, 1976

[30] Foreign Application Priority Data

Mar. 12, 1975 Japan .................................. 50-29105

[51] Int. Cl.² ............................................ A61K 39/02
[52] U.S. Cl. ...................................................... 424/92
[58] Field of Search .......................................... 424/92

[56] References Cited

U.S. PATENT DOCUMENTS 3,928,565 12/1975 Homma et al. ......................... 424/92

Primary Examiner—Sam Rosen
Attorney, Agent, or Firm—Blum, Moscovitz, Friedman & Kaplan

[57] ABSTRACT

Mink infection caused by *Pseudomonas aeruginosa* can be prevented by administering to mink a prophylactic preparation in the form of vaccine whose effective component is a compound mainly consisting of protein and a small amount of lipid and sugar derived from *Pseudomonas aeruginosa*.

4 Claims, No Drawings

PROPHYLACTIC PREPARATION FOR TREATING MINK INFECTION CAUSED BY *PSEUDOMONAS AERUGINOSA*

BACKGROUND OF THE INVENTION

Pseudomonas aeruginosa is known to be naturally resistant against most of the antibiotics commonly used, and the use of antibiotics for the prophylactic treatment of infection due to bacteria is almost completely ineffective when the hosts are physiologically immature in immune response or in those cases where hosts are being treated by administration of medicines which decrease their immune protective mechanisms.

Since mink hemorrhagic pneumonia is endemic and caused by a single serotype strain, formalin-killed cells were prepared from cultures of the homologous serotype strain which had been isolated from mink which had died due to the endemic, with a view to developing a protective or preventive agent. For the purpose of protecting mink from the contagious disease, minks were immunized with the formalin-killed cells. However, the therapeutic effects were doubtful.

Actually, those antibiotics to which the bacteria are sensitive cannot readily be administered repeatedly to minks at 2-3 days' intervals because the number of minks to be processed is so great. The cost of the drug is another reason for the unsuitability of repeated administration of the drug to this species. Even when adopted, therapy by antibiotics is generally ineffective, because most of minks are kittens whose immune system is physiologically immature. Another reason is that a few administrations of the drug are not effective enough for preventing the natural development of the disease.

For bovine mammitis, there was a case in which antibiotics were administered continuously, but the effect achieved by administration for a lengthy period was actually not worth the cost of the drug. An acute case may be handled, but chronic cases could hardly be treated in most cases. The radical treatment of mastitis due to Pseudomonas aeruginosa cannot be achieved by antibiotic treatment alone and relapses of this infection occur after temporary success of the treatment.

On the other hand, immunization is an important factor for protecting hosts from infection due to Pseudomonas aeruginosa. As a vaccine, a thermostable O antigen of glycolipid derived from Pseudomonas aeruginosa is known, but this O antigen has the disadvantage that it exhibits a protective activity only against infection due to bacterial strains of the same serotype as that of the strain from which the vaccine was prepared.

As is evident a better method of protection of animals against infection by Pseudomonas aeruginosa is still needed.

SUMMARY OF THE INVENTION

An effective prophylactic preparation for protection of mink against infection by Pseudomonas aeruginosa is a vaccine derived from Pseudomonas aeruginosa. The effective component of the vaccine is a lipoprotein and is accompanied by a small quantity of a lipid and sugar. A method of preparing the vaccine termed OEP herein is described in British Patent No. 1,365,950 in which patent the product is termed CWP.

OEP may be used by itself as the inoculum or injected with either KA (potassium alum) or FIA (Freund's Incomplete Adjuvant). The method of prophylactic protection of mink consists of administration of a single dose of 50 - 1,000 $\mu$g/kg the basis of the preparation being OEP. Preferably the preparation should be inoculated twice at an interval of three weeks.

Accordingly, an object of the present invention is to provide a prophylactic preparation for preventing mink infection by Pseudomonas aeruginosa.

Another object of the present invention is to provide a method of preventing mink infection by Pseudomonas aeruginosa.

Still other objects and advantages of the invention will in part be obvious and will in part be apparent from the specification.

The invention accordingly comprises the several steps and the relation of one or more of such steps with respect to each of the others, and the composition possessing the features, properties, and the relation of constituents, which are exemplified in the following detailed disclosure, and the scope of the invention will be indicated in the claims.

DESCRIPTION OF THE PREFERRED EMBODIMENTS

The present invention provides a prophylactic preparation in a form of a vaccine for mink against Pseudomonas aeruginosa and a prophylactic method for the application thereof.

The vaccine activity of OEP provides protection against infection regardless of the serotype of Pseudomonas aeruginosa, and this OEP possesses also non-specific protection against infection due to Pseudomonas aeruginosa as well as by other bacteria (Japan G. Exp. Med., 41, 489-492, 1971); it also has an antitumor activity (Gann, 64, 523-525, 1973) and interferon-inducing activity (Japan G. Exp. Med., 41, 493-496, 1971).

OEP which produces a vaccine is an effective component of a prophylactic preparation in the present invention; it can be obtained by isolating a protein fraction of Pseudomonas aeruginosa, but does not contain, in principle, O antigen involved in glycolipid, and is therefore essentially different in such a respect from endotoxin combined with thermostable O antigen so far employed.

The following is an example indicating the chemical content of OEP:

| | |
|---|---|
| N | 13.8% |
| P | 1.17 |
| Sugar (Anthrone) | 0.01 |
| Hexosamine (Elson-Morgan) | 0.03 |
| KDO | 0.3 |
| Protein | 85 |

The following is an example of an analysis indicating the amino acid content of the protein:

| | |
|---|---|
| Glycine | 5.2% (mol.) |
| Alanine | 8.7 |
| Valine | 6.9 |
| Leucine | 9.8 |
| Isoleucine | 5.1 |
| Serine | 4.0 |
| Threonine | 4.9 |
| Tyrosine | 3.8 |
| Phenylalanine | 4.7 |
| Methionine | 2.3 |
| Proline | 4.0 |
| Asparagine | 9.1 |
| Glutamine | 14.3 |
| Histidine | 2.4 |
| Arginine | 6.7 |
| Lysine | 7.4 |

The above OEP can be prepared, for instance, by the method described in the British Pat. No. 1,365,950; the product abbreviated as CWP in the above British Patent is equivalent to OEP referred to herein. Said British Patent is incorporated by reference. OEP can be inoculated by itself or injected with either KA (potassium alum) or FIA (Freund's Incomplete Adjuvant).

A prophylactic preparation referred to in the present invention contains the above vaccine as an effective component and can be obtained by mixing diluents used in general such as phosphorous buffer solution and the like. It is desirable to inoculate the above prophylactic preparation in mink in a single dose of 50 – 1,000 μg/kg based on OEP. A sufficient prophylactic effect can be obtained, for instance, by inoculating the preparation twice at an interval of three weeks.

The present invention is further illustrated by the following example:

EXAMPLE

Minks were immunized by subcutaneous administration twice at an interval of three weeks, and were challenged intranasally 2 or 3 weeks thereafter. They were sacrificed for autopsy after observation for approximately one month after the challenge. OEP was isolated from strain N 10, which belongs to serotype 5. The strains used for the challenge were heterologous ones; strain NO5 belongs to serotype 8, while strain NC5 belongs to serotype 5.

Table 1 shows the effect of OEP vaccination on protection of mink against challenge with each of two kinds of strains, NC5 and NO5.

TABLE 1

EFFECT OF OEP VACCINATION ON PROTECTION OF MINK AGAINST CHALLENGE WITH EACH OF TWO KINDS OF STRAINS, NC5 AND NO5

| Name of strain | Dose used for challenge | Weight of inoculated OEP (mg/each animal) | No. of dead animals / No. of infected animal |
|---|---|---|---|
| NC 5 | $3 \times 10^{10}$ | 0.1 | 4/5 |
|  |  | 0.5 | 3/5 |
|  |  | 2.5 | 0/5 |
|  |  | 0 | 4/5 |
| NO 5 | $7 \times 10^{6}$ | 4 | 1/20 |
|  |  | 2 | 3/20 |
|  |  | 0 | 10/20 |
|  | $3 \times 10^{8}$ | 0.1 | 0/5 |
|  |  | 0.5 | 0/5 |
|  |  | 2.5 | 3/5 |
|  |  | 0 | 0/5 |

As shown in Table 1, the results clearly showed that the immunized mink could be protected from infection caused by the challenge with both of the two strains, NC5 and NO5.

The same serotype strains as that used for the challenge could be recovered from all the dead minks. The severity of the hemorrhagic pneumonitis was remarkable. On the other hand, no bacterium could be isolated from organs and blood of the sacrificed mink which had survived for approximately one month after the challenge. No pathologic sign of hemorrhagic pneumonitis in their lungs could be found on autopsy.

Table 2 shows the results of intranasal challenge carried out on minks which had been immunized with OEP and which recovered from the previous infections due to live bacteria (strain NO5) administered intranasally. Since $LD_{50}$ is $10^6$ strains, it can be realized that minks are now sufficiently protected from infection from intranasal administration of 10,000 $LD_{50}$ dose of the bacteria.

TABLE 2

THE RESULTS OF INTRANASAL CHALLENGE WITH A LARGE DOSE OF NO5 STRAIN ON MINK WHICH HAD BEEN IMMUNIZED WITH OEP, AND RECOVERED FROM PREVIOUS INFECTIONS DUE TO LIVE BACTERIA

| Amount of IMMUNIZING dose OEP (mg/capita) | Challenge dose (Numbers of bacteria) | | | | | |
|---|---|---|---|---|---|---|
|  | $2.2 \times 10^{10}$ | | | $2.2 \times 10^{9}$ | | |
| 4 | 0 | 0 | $\phi_2$ | 0 | 0 | $\phi_1$ |
| 2 | 0 | 0 | 0 | 0 | 0 | 0 |
| 1 | 0 | 0 | $\phi_2$ | 0 | $\phi_3$ | $\phi_1$ |
| 0 | $\phi_2$ | $\phi_2$ | $\phi_2$ | $\phi_2$ | $\phi_3$ | $\phi_2$ |

Note:
0 indicates minks which survived.
φ indicates minks which died from challenging. Subscript indicates day on which minks died after challenging.

Table 2 indicates that the geometrical average values of OEP-HA antigen of 10 animals of each group immunized with the dose of 4 mg or 2 mg of OEP were equally 394 times, and the same of control groups was less than 40 times. This means that OEP-HA values could be correlative to OEP immunity, and they could also be a kind of criterion indicating the capability of OEP in preventing infection by Pseudomonas aeruginosa.

It will thus be seen that the objects set forth above, among those made apparent from the preceding description, are efficiently attained and, since certain changes may be made in carrying out the above method and in the composition set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A method of preventing mink infection by Pseudomonas aeruginosa by immunizing said mink with a dose of 50 – 4,000 μg/kg of a prophylactic preparation (on the basis of OEP) in the form of a vaccine whose effective component consists mainly of protein and a small amount of lipid and sugar derived from Pseudomonas aeruginosa.

2. A method of preventing mink infection by Pseudomonas aeruginosa as defined in claim 1, wherein said preparation is injected into any part of the whole body.

3. A method of preventing mink infection by Pseudomonas aeruginosa as defined in claim 1, wherein said dose is administered twice at an interval of 2 to 3 weeks.

4. A method of preventing mink infection by Pseudomonas aeruginosa as defined in claim 1, wherein said dose is administered in combination with potassium alum or Freund's Incomplete Adjuvant.

* * * * *